United States Patent
Kim et al.

(10) Patent No.: US 10,393,738 B2
(45) Date of Patent: Aug. 27, 2019

(54) MULTI-WELL CUVETTE PROVIDED WITH INTEGRATED REACTION AND DETECTION MEANS

(71) Applicant: Boditech Med Inc., Chuncheon-si, Gangwon-do (KR)

(72) Inventors: Byeong-Chul Kim, Chuncheon-si (KR); Bong-Sok Moon, Namyangju-si (KR); Won-Hee Lee, Chuncheon-si (KR); Chan-Young Jeon, Chuncheon-si (KR)

(73) Assignee: Boditech Med Inc., Chuncheon-Si, Gangwon-Do (KR)

( * ) Notice: Subject to any disclaimer, the term of this patent is extended or adjusted under 35 U.S.C. 154(b) by 135 days.

(21) Appl. No.: 15/035,436

(22) PCT Filed: Nov. 11, 2014

(86) PCT No.: PCT/KR2014/010784
§ 371 (c)(1),
(2) Date: May 9, 2016

(87) PCT Pub. No.: WO2015/072718
PCT Pub. Date: May 21, 2015

(65) Prior Publication Data
US 2016/0291009 A1    Oct. 6, 2016

(30) Foreign Application Priority Data

Nov. 12, 2013   (KR) .................. 10-2013-0136620
Nov. 11, 2014   (KR) .................. 10-2014-0155885

(51) Int. Cl.
*G01N 33/558*   (2006.01)
*B01L 3/00*   (2006.01)
(Continued)

(52) U.S. Cl.
CPC ............ *G01N 33/558* (2013.01); *B01L 3/502* (2013.01); *B01L 3/5023* (2013.01);
(Continued)

(58) Field of Classification Search
CPC ............ G01N 33/558; G01N 30/6091; G01N 2030/8813; B01L 3/502; B01L 2300/0627;
(Continued)

(56) References Cited

U.S. PATENT DOCUMENTS 4,956,148 A      9/1990  Grandone
5,075,077 A  *  12/1991  Durley, III ............ B01L 3/545
                                                               422/424
(Continued)

FOREIGN PATENT DOCUMENTS

JP    2001-318101 A    11/2001
KR    20-0299628 Y1    1/2003
(Continued)

OTHER PUBLICATIONS

International Search Report dated Feb. 17, 2015 of PCT/KR2014/010784 which is the parent application and its English translation—5 pages.

(Continued)

*Primary Examiner* — Dennis White
(74) *Attorney, Agent, or Firm* — Knobbe Martens Olson & Bear LLP

(57) ABSTRACT

The present application discloses a multi-well cuvette for integrating the reaction between a sample and a reagent with the detection of a specific analyte included therein, and the multi-well cuvette comprises: a reaction chamber part having a sample and a reagent placed therein; and a detection part for detecting the reaction between the sample and the reagent, wherein the reaction chamber part comprises: an (Continued)

extraction member standby chamber in which a member for dividing or distributing the sample is on standby; a sample filling chamber; and a reagent filling chamber which is filled with the reagent, and in which the reaction with the sample is carried out, wherein the detection part comprises: a chromatography analysis means for a reactive product between the sample and the reagent; and a detection chamber for accommodating the same.

17 Claims, 8 Drawing Sheets

(51) Int. Cl.
  *G01N 30/60* (2006.01)
  *G01N 30/88* (2006.01)
(52) U.S. Cl.
  CPC .... *G01N 30/6091* (2013.01); *B01L 2200/027* (2013.01); *B01L 2200/10* (2013.01); *B01L 2200/16* (2013.01); *B01L 2300/021* (2013.01); *B01L 2300/044* (2013.01); *B01L 2300/0627* (2013.01); *B01L 2300/087* (2013.01); *B01L 2300/0825* (2013.01); *B01L 2400/0406* (2013.01); *G01N 2030/8813* (2013.01)
(58) Field of Classification Search
  CPC ......... B01L 2200/10; B01L 2400/0406; B01L 2300/087; B01L 2300/021; B01L 2300/044; B01L 3/5023; B01L 2200/16; B01L 2200/027; B01L 2300/0825
  See application file for complete search history.

(56) References Cited

U.S. PATENT DOCUMENTS

| | | | |
|---|---|---|---|
| 6,333,008 B1 * | 12/2001 | Leistner | G01N 21/03 422/52 |
| 6,410,275 B1 | 6/2002 | Kluttz et al. | |
| 2006/0120926 A1 | 6/2006 | Takada et al. | |
| 2006/0275922 A1 * | 12/2006 | Gould | B01L 3/5023 436/514 |
| 2007/0148780 A1 | 6/2007 | Murata et al. | |
| 2011/0262919 A1 | 10/2011 | Tajima | |
| 2013/0161190 A1 | 6/2013 | Ewart et al. | |
| 2013/0183769 A1 | 7/2013 | Tajima | |

FOREIGN PATENT DOCUMENTS

| | | |
|---|---|---|
| KR | 10-2003-0065341 A | 8/2003 |
| KR | 10-0401389 B1 | 10/2003 |
| KR | 10-2008-0038093 A | 5/2008 |
| KR | 10-2011-0007699 A | 1/2011 |
| KR | 10-2011-0127386 A | 11/2011 |
| KR | 10-1149357 B1 | 5/2012 |
| WO | 90/14161 A1 | 11/1990 |

OTHER PUBLICATIONS

Extended European Search Report & Amended Claims of corresponding Patent Application No. 14862520.5—14 pages (Jul. 3, 2017).

* cited by examiner

MULTI-WELL CUVETTE PROVIDED WITH INTEGRATED REACTION AND DETECTION MEANS

BACKGROUND

Field of the Invention

The present disclosure relates to a multi-well cuvette for use in detection and analysis of a particular component in samples such as biological samples.

Description of the Related Art

Continuous developments of technology in the medical and related fields have made it possible that various biological materials such as blood cells, nucleic acid molecules, proteins and antigens and the like are routinely tested in a number of biological samples such as blood. Generally performed in the analysis are steps of obtaining a suitable biological sample, which is then used for a reaction with a proper reagent(s) to detect the presence or absence, and/or to measure the amount of a particular analyte of interest to provide information for diagnosis a disease or determine the status of a particular disease.

To obtain reliable and reproducible results in such processes, it is necessary that the reagents used in the reactions as well as the biological samples to be tested are not influenced by the external conditions. It is important that an application of an accurate amount of sample each time the reaction is performed. But it is likely that the biological samples or reactants may be accidentally exposed to air or contaminated with unwanted materials in addition to the inaccurate amount of samples applied.

Also the problems such as cross-contamination between samples, or application of inaccurate amount of samples and the like frequently arise in the conventional process, in which cases, the reaction between the sample and reagents; and the detection of the reaction results are generally performed in separate devices.

Therefore a need exists for a convenient and reliable device integrating means for reaction between a sample and reagents; and means for detecting the result therefrom to improve the accuracy and reproducibility as well as to reduce the steps and cost required.

KR Patent Application Publication NO. 10-2007-7031051 published May 2, 2008 relates to a cuvette and a method and shaping tool for manufacture thereof and discloses a cuvette for obtaining and providing sample to an analyzer.

SUMMARY

The present disclosure is to provide a device integrated therein the means for reaction between a sample and reagents; and the means for detecting the result therefrom.

It is therefore an aspect of the present invention to provide a multi-well cuvette with an integrated reaction and detection means, which may comprise: a reaction part for a reaction between a biological sample and a reagent comprising a collector receiving chamber to accommodate a collector for collecting and dispensing the biological sample, the reagent and/or the mixture thereof; a sample chamber to accommodate the biological sample; and at least one reagent chamber to accommodate the reagent where a reaction between the sample and the reagent are performed, the collector receiving chamber, the sample chamber and the at least one reagent chamber being arranged in a row; and an analysis part for detecting a reaction product between the biological sample and the reagent comprising a chromatographic system and a detection chamber accommodating the chromatographic system, the analysis part being extended from an end of the reaction part.

In the foregoing multi-well cuvette, the chromatographic system enclosed is a chromatographic cartridge for lateral flow assay.

Still in the foregoing multi-well cuvette, the chromatographic cartridge comprises a base member; and a cover member covering an upper portion of the base member, wherein the base member comprises a strip receiving part being configured to accommodate a strip used for a lateral flow assay and a sample receiving well being configured to accommodate the reaction product, the sample receiving well being extended from an one end of the strip receiving part, wherein the cover member comprises a sample inlet through which the reaction product is introduced into and fills the sample receiving well, the sample inlet being formed in a position being opposite to the sample receiving well when the cover member covers the base member; and a measurement window formed in a position being opposite to the strip receiving part when the cover member covers the base member, wherein at least one of the base member and the cover member comprise a structure for introducing the reaction product loaded in the sample receiving well to the strip by an capillary action, the structure on the cover member being formed on the lower part thereof adjacent to the sample inlet, the structure on the base member being formed inside the sample receiving well.

Further still in the foregoing multi-well cuvette, the detection chamber further comprises a separation member positioned under the sample receiving well. The separation member is to separate or to remove any unwanted or undesired material from the reaction products to improve the analysis quality and is for example a magnetic member which includes a magnet and a holder for accommodating the magnet.

Further still in the foregoing multi-well cuvette, the collector receiving chamber and the sample chamber have an open upper portion through which a tip installed in the test device which may be used with the present multi-well cuvette can move into the chamber.

Further still in the foregoing multi-well cuvette, one or more of the sample and/or reagent chambers may be included in the reaction part. In cases where two or more chambers are included, each chamber of the sample chambers may include a sample of identical or different, and likewise each chamber of the reagent chambers may include a reagent of identical or different.

Further still in the foregoing multi-well cuvette, the upper portion of the reagent chamber may be covered with a first cover. In one embodiment, the first cover may be formed of a thin material such as membrane so that a tip installed in the test device which may be used with the present multi-well cuvette can penetrate the membrane and move into the chamber.

Further still in the foregoing multi-well cuvette, a second cover covering at least a portion of the upper portion of the multi-well cuvette is included. In one embodiment, the present multi-well cuvette may be used with the cover closed in place.

Further still in the foregoing multi-well cuvette, the second cover may further comprise a barcode at any appropriate position not preventing the operation or test using the present cuvette to distinguish a type of the biological sample being tested. The present multi-well cuvettes enable an accurate as well as a rapid analysis of analytes included in a sample. That is, a sample in the sample chamber is collected by a collecting means such as a tip located in the collector receiving chamber from which the collecting means is pick up by a device with a moving part, and then the sample is delivered to the reagent chamber in which the sample is mixed with the reagent in the chamber and they are allowed for a reaction to occur. After then, the reaction products are introduced to the detection part and the analytes of interest are detected quantitatively and/or qualitatively by a lateral flow chromatographic assay.

It is an advantage of some of the above aspects of the invention that such processes are all performed in the present multi-well cuvette comprising all the components required to perform the appropriate processes. The elements or components of the cuvette are serially arranged in a row, thus, when the multi-well cuvette is used with a test device, the test can be performed by moving the present cuvette in one direction along a straight line.

It is a further advantage of some of the above aspects of the invention that in the present multi-well cuvette, a collector receiving chamber, a sample chamber, a reagent chamber and a detection chamber are sequentially arranged in a row such that collecting of a sample, mixing and reacting the sample with a reagent and detecting the reaction products can be sequentially performed. Thus a test device used with the present multi-well cuvette is simplified by needing to move the cuvette only in one direction.

Thus, when the tests are performed using the present cuvettes, the test device with simpler structures can be employed, which enables a convenient and rapid test.

It is a further advantage of some of the above aspects of the invention that in the present multi-well cuvette, a collector receiving chamber, a sample chamber, a reagent chamber and a detection chamber are sequentially arranged in a row and integrated into a single device leading to a cuvette with simpler structures. Thus the cost of manufacturing can be reduced.

It is a further advantage of some of the above aspects of the invention that by integrating the chambers used for the reaction and the detection of the reaction products in one device, the problems with a conventional chromatographic method in which the reaction process and the detection of the reaction products are performed in separate devices resulting the cross-contamination between reagents and/or inaccurate amount of sample loading can be avoided.

BRIEF DESCRIPTION OF THE DRAWINGS

The above and other aspects, features and advantages of the present invention will become more apparent from the following detailed description when taken in conjunction with the accompanying drawings in which.

DETAILED DESCRIPTION OF EMBODIMENTS

Figure 1:
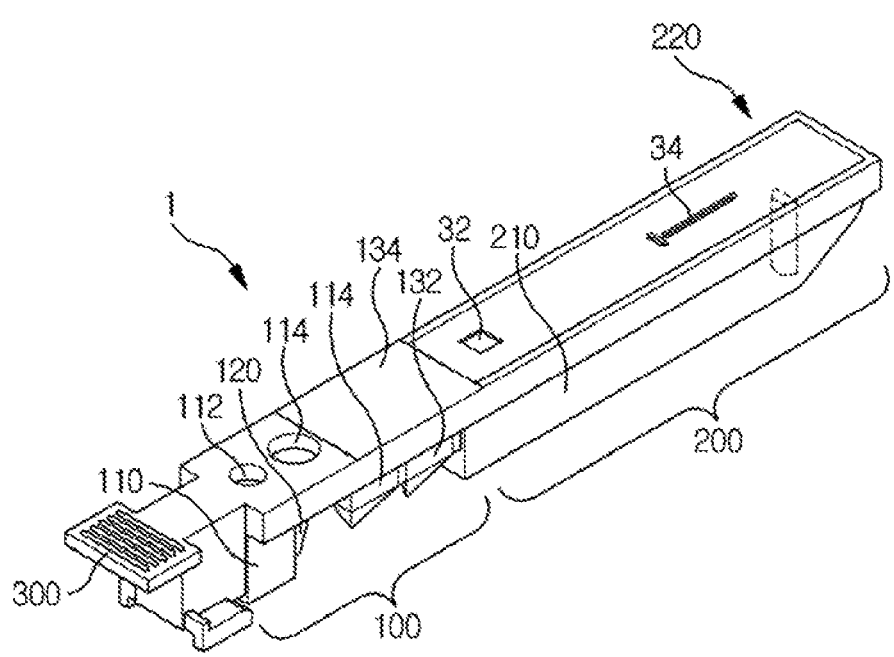
FIG. 1 is a schematic diagram of a perspective view of a multi-well cuvette according to one embodiment.

Reference will now be made in detail to the present embodiments, examples of which are illustrated in the accompanying drawings, wherein like reference numerals refer to the like elements throughout. In this regard, the present embodiments may have different forms and should not be construed as being limited to the descriptions set forth herein.

Spatially relative terms, such as "beneath", "below", "lower", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" can encompass both an orientation of above and below. The device may be otherwise oriented.

In the figures, the size or thickness of some of the elements is depicted exploded or omitted or schematically depicted for clarity and convenience of explanation. Also the size and area of some of the elements may not represent the actual size or area of the elements.

Also, the angles or directions or orientations mentioned in the present disclosure while explaining the present elements are based on the figures of the present disclosure. Reference will be made to the figures when the reference point for an angle or the relationship among various elements of the present disclosure are not clearly indicated.

In the drawings, the dimensions of structures are exaggerated for clarity of the inventive concept. The size and area of each element may be different from an actual size and area.

In addition, the directions mentioned at the time of describing the structure of the inventive concept are based on the directions illustrated in the drawings. In the descriptions about the structure of the inventive concept, when a reference point and a positional relationship are not clearly defined, the relevant drawings will be referenced.

Figure 2A:
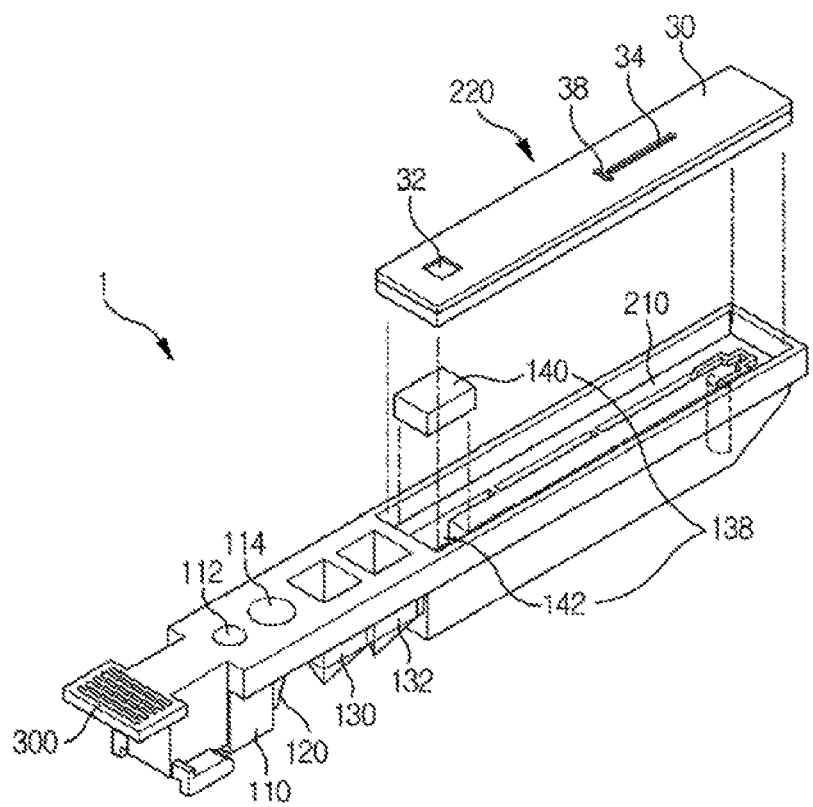
FIG. 2A is a schematic diagram of an exploded perspective view of a multi-well cuvette according to one embodiment.
Figure 2B:
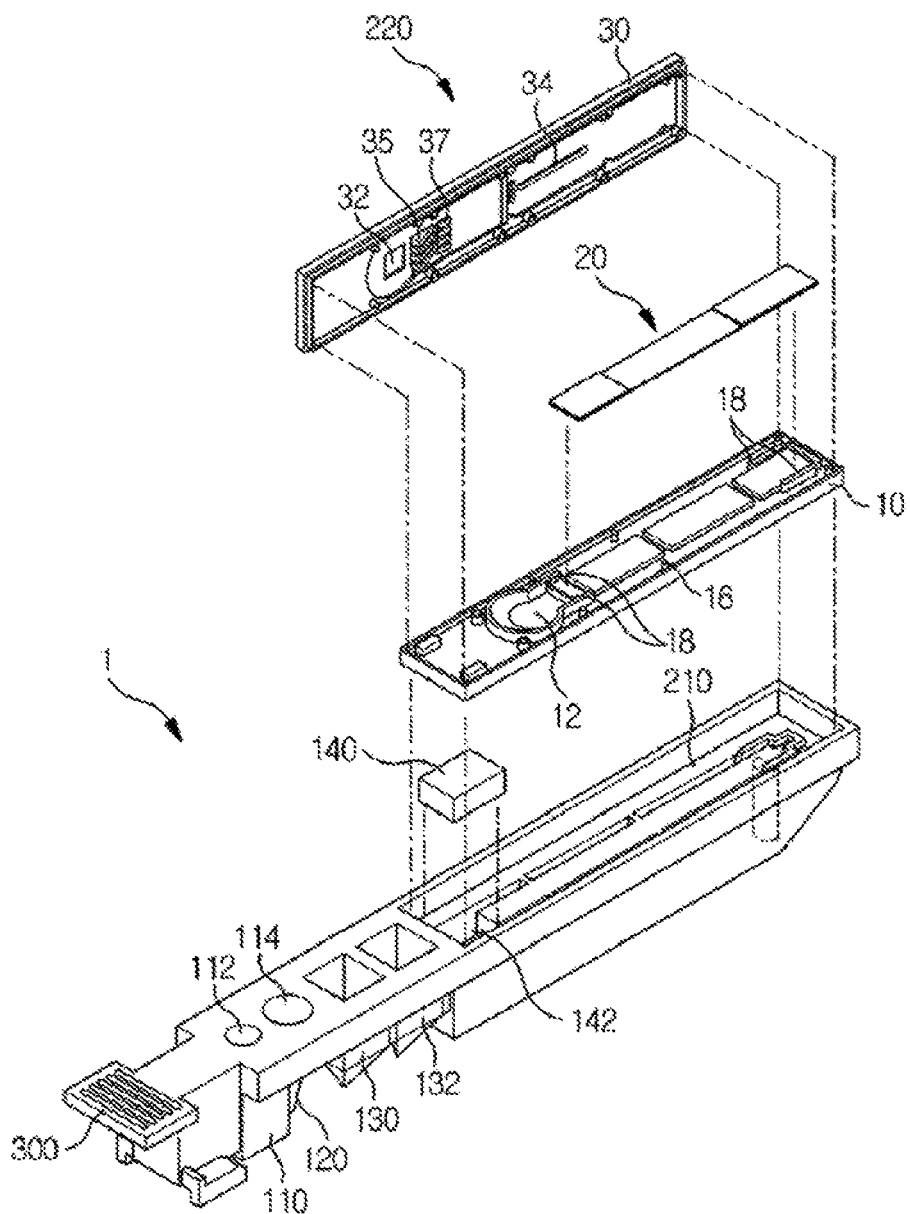
FIG. 2B is a schematic diagram of an exploded perspective view of a multi-well cuvette according to one embodiment in which the chromatographic cartridge is shown as exploded view.

FIG. 1 is a perspective view of a multi-well cuvette (1) that is an integrated device for performing reaction between a sample and a reagent and analyzing the reaction product, according to one embodiment of the present disclosure. FIGS. 2A and 2B is an exploded perspective view of a multi-well cuvette (1) according to one embodiment of the present disclosure.

The multi-well cuvette according to the present disclosure is advantageously used for detecting and/or analyzing an analyte in a sample. The term "sample" in the present disclosure refers to a material comprising an analyte of interest to be test or a material suspected of containing an analyte of interest to be tested. The sample which may be employed in the present disclosure takes a form of a liquid or a fluid or semi-solid. In one embodiment, biological samples, that is, samples of a biological origin, such as blood, a plasma, a serum, a urine, a saliva, a feces, and cell or tissue extracts are employed.

The term "analyte" as used herein refers to a component or a compound or a material present in the sample to be tested and may also be referred to a "target". Examples of the analytes include, but are not limited to a protein or a nucleic acid molecule without limitation. The proteins include polypeptide, oligopeptides and peptides of synthetic or natural origin. The nucleic acids include a genomic DNA or a fragment thereof, cDNA and oligonucleotides and RNA of synthetic or natural origin. Also included in the nucleic acids are single or double stranded DNAs. Such nucleic acid molecules may be prepared or synthesized using conventional methods known in the art.

In one embodiment of the present disclosure, as analytes, proteins such as hsCRP (high sensitivity C-reactive protein), MicroCRP, HbA1c (Glycated hemoglobin), microalbumin, PSA (prostate specific antigen), AFP (Alpha-fetoprotein), cTnI (Cardiac Troponin I) are tested or detected.

The reagents employed in the analysis using the present cuvette refers to materials or compounds suitable for analyzing the analytes of interest and may vary depending on the particular analytes to be tested or detected. For example, such reagents may include an antibody specifically binding to a corresponding antigen but are not limited thereto.

According to one embodiment of the present disclosure, the multi-well cuvette (1) comprises a reaction part (100) to accommodate a reagent and a biological sample for a reaction between the sample and the reagent; and an analysis part (200) for detecting a reaction product between the biological sample and the reagent, in which a reaction part (100) comprises a collector receiving chamber (110) to accommodate a collector for collecting and dispensing the biological sample, the reagent and/or the mixture thereof; a sample chamber (120) to accommodate the biological sample; and at least one reagent chamber (130) to accommodate the reagent where a reaction between the sample and the reagent are performed, and the analysis part (200) comprises a chromatographic detection system and a detection chamber (210) accommodating the chromatographic system, the analysis part being extended from an end of the reaction part.

The reaction part (100) of the multi-well cuvette (1) according to the present disclosure is configured to have a plurality of chambers or wells to accommodate various biological samples comprising or being expected to comprise a target(s) or an analyte(s) of interest and to accommodate particular reagent(s) suitable for a reaction with the biological sample. Thus, the reaction part (100) has a structure in which a plurality of wells arranged in a row and each of the wells is separated from each other by a wall to prevent reagents and biological samples from being unnecessarily mixed together before a reaction. That is, the reaction part (100) comprises a plurality of wells. Also more than one reaction part (100) may be included in the present multi-well cuvette (1).

The reaction part (100) of the multi-well cuvette (1) according to the present disclosure is configured to comprise a collector receiving or stand-by chamber (110) to accommodate a collector for collecting and dispensing a biological sample, a reagent and/or the mixture thereof; a sample chamber (120) to accommodate a biological sample; and at least one reagent chamber (130) to accommodate a reagent where a reaction between the sample and the reagent are carried out. As described herein before, the collector receiving or stand-by chamber (110), the sample chamber (120); and at least one reagent chamber (130) are arranged in a row and configured to have a well structure separated from each other by a wall structure to prevent the unnecessary mixing of the materials contained therein. The at least one reagent chamber (130) may comprise at least one reagent suitable for reaction, detection and/or analysis of the target or analytes of interest in biological samples. A reaction between a biological sample and reagents contained in a reagent chamber (130) start when the biological sample is introduced or injected into the reagent chamber (130) from a sample chamber (120). Also the multi-well cuvette (1) according to the present disclosure may comprise a plurality of reagent chamber (130), in which case each reagent chamber or well may comprises a reagent(s) of identical or different, or not all the wells or chambers may contain a reagent and some of the wells or chambers may be left empty or not in use. In one embodiment, a first (131) and a second (132) reagent chambers are included without being limited thereto.

The analysis part (200) of the multi-well cuvette according to the present disclosure is configured to comprise a chromatographic detection system for detecting a reaction product between a biological sample and a reagent in the reaction part (100); and a detection chamber accommodating the chromatographic system. The analysis part (200) is configured to be extended from an end of the reaction part. In one embodiment, as a chromatographic system, a cartridge for a lateral flow assay is used.

A lateral flow assay is a method for quantitatively and/or qualitatively measuring a particular analyte such as nucleic acids or proteins contained in a sample. In the lateral flow assay, a reaction product or a sample is applied to a strip (20) comprising a cellulose nitrate membrane (medium for development or separation of analytes in the sample) to which an antibody and/or an antigen and/or an oligonucleotide specifically binding to the analyte of interest are coupled at a certain location. Then the sample applied migrates through the membrane by a chromatographic flow during which a protein or analyte of interest is captured by corresponding antigen or antibody, or oligonucleotide forming a complex in the membrane which is then detected. For detailed explanations, Korean Patent application publication Nos. 2003-0065341, 2011-0007699, 2011-0127386, and Patent publication No. 1149357 may also be referred.

Referring to FIGS. 2A and 2B, the detection chamber (210) comprises a cartridge suitable for a lateral flow assay. According to one embodiment of the present disclosure, chromatographic cartridge (200) comprises a base member; and a cover member covering an upper portion of the base member wherein the base member comprises a strip receiving part configured to accommodate a strip comprising a development medium used for a lateral flow assay; and a sample receiving well configured to accommodate a reaction product, the sample receiving well being extended from an one end of the strip receiving part. Examples of the cartridge which may be employed for the present disclosure may comprise ones disclosed in Korean Patent application publication Nos. 2003-0065341, 2011-0007699, 2011-0127386, and Patent publication No. 1149357 may also be referred.

Figure 4:
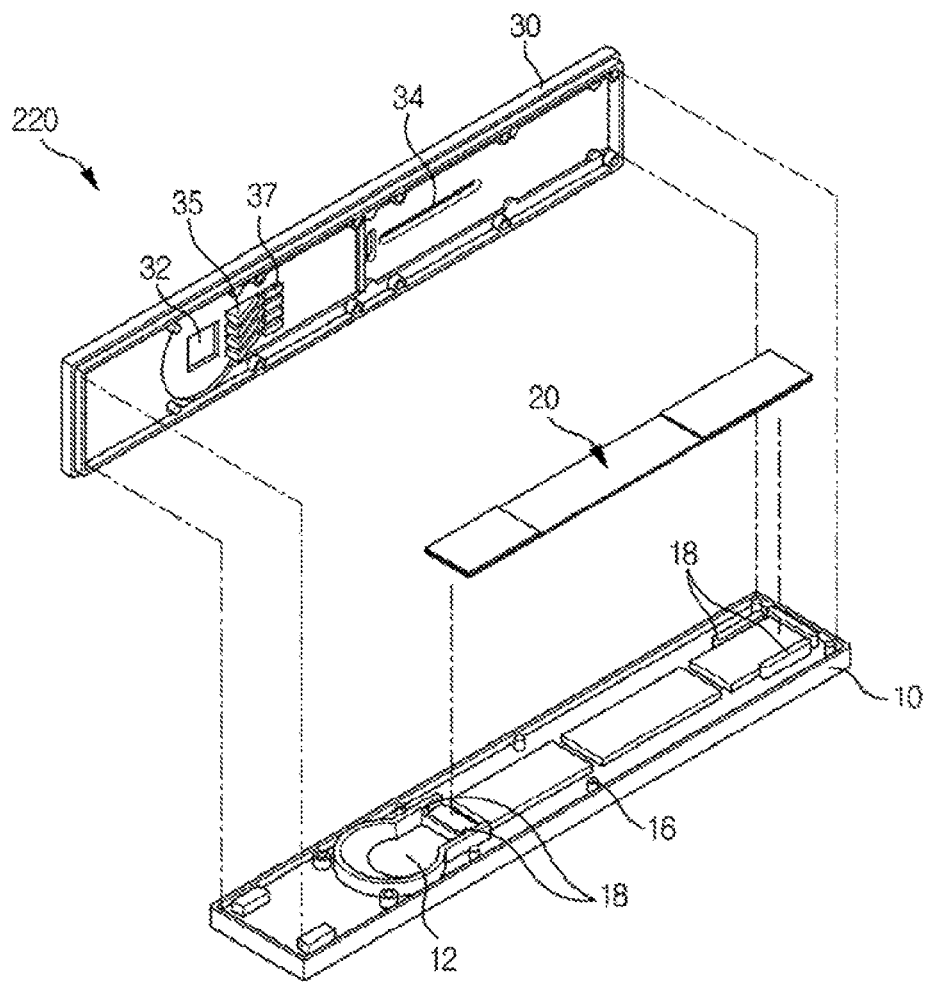
FIG. 4 is a schematic diagram of an exploded perspective view of a chromatographic cartridge for lateral flow assay employed in the present multi-well cuvette according to one embodiment.

Referring to FIG. 4, the cartridge (220) is installed or fit into a detection chamber (210) and comprises a cover member (30) and a base member (10). A reaction product is introduced into a well (12) through a sample inlet (32) formed in the cover member. The sample loaded in the well (12) is then transferred or delivered or introduced to a strip (20) by a capillary action through a structure (35, 37) formed on the lower side of the cover member and/or the upper side of the base member at a position corresponding to the one on the cover member, particularly inside the sample well (12). Specifically, the cartridge for a lateral flow assay which may be comprised in the present multi-well cuvette comprises a base member (10); and a cover member (30) covering an upper portion of the base member. The base member (10) comprises a strip receiving part (18) configured to accommodate a strip used for a lateral flow assay; and a sample receiving well (12) configured to accommodate a reaction product and is formed being extended from a one end of the strip receiving part. The cover member (30) comprises a sample inlet (32) through which the reaction product is introduced into and fills the sample receiving well (12) which is formed in a position being opposite to the sample receiving well when the cover member covers the base member; and a measurement window (34) for detection of the development which is formed in a position being opposite to the strip receiving part when the cover member covers the base member. The cover member further comprises an air inlet (38) if needed. A structure(s) (35, 37) for inducing capillary action is formed on the lower side of the cover member and/or on the upper side of the base member in the sample receiving well (12). In one embodiment, the structure(s) (35, 37) for inducing capillary action on the lower side of the cover member are formed being adjacent to the sample inlet and the structure on the base member is formed inside the sample receiving well.

The sample inlet (32) is formed at a position in the cover member which is directly opposite to the sample receiving well (12). When the cover member (30) closes the base member, they interlock with each other through coupling means such as protrusions or receptacles being dimensioned to mutually intercouple so that the cartridge becomes substantially waterproof or sealed aerosol proof. Also the strip receiving well may comprises at least one guide prevent the strip from moving so that to the strip mounted thereon kept in a fixed position.

The reaction product introduced through a sample inlet (32) to a sample receiving well (12) may be transferred to a strip (20) by a variety of methods. In one embodiment of the present disclosure, the reaction product migrates to a strip by a capillary action. For this, in one embodiment, fine channels are formed at a position between a sample receiving well (12) and a stripe receiving part (18), or inside a sample receiving well (12), and through which, the reaction product is then transferred to a strip and lateral flow is initiated. Other examples include a case in which one end of the strip may directly contact with the sample or reaction product in the sample receiving well to initiate a lateral flow.

The multi-well cuvette according to the present disclosure may further comprises a magnetic member (138) positioned under the sample receiving well (12). The magnetic member comprises a magnet (140) and a magnet well (142) to accommodate the magnet. The magnetic member is for removing any unwanted material from the reaction products before it being analyzed by a chromatographic assay. For this, magnetic beads with antibodies being attached thereto are present in the reagent chamber (130) and the antibodies specifically bind to unwanted materials of interest to be removed. The unwanted materials to be removed include for example red blood cells of whole blood. When whole blood is used as a biological sample and magnetic beads are employed, the reaction product between a biological sample and a reagent comprises magnetic beads coated with antibodies specific for RBCs to remove them. During and after the process or reaction, RBCs become attached to the magnetic beads through the antibodies and the magnetic beads are then precipitated together with RBC attached thereto when they are in contact with the magnet (140) of the magnetic member thus eliminating RBCs from being analyzed by a chromatographic assay.

Figure 5A:
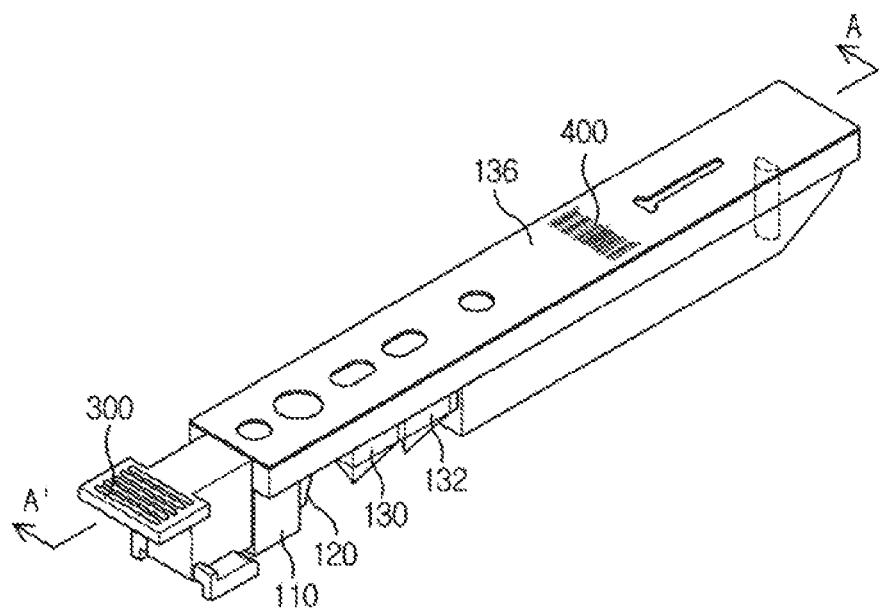
FIG. 5A is a schematic diagram of a perspective view of a multi-well cuvette comprising a second cover according to one embodiment.
Figure 5B:
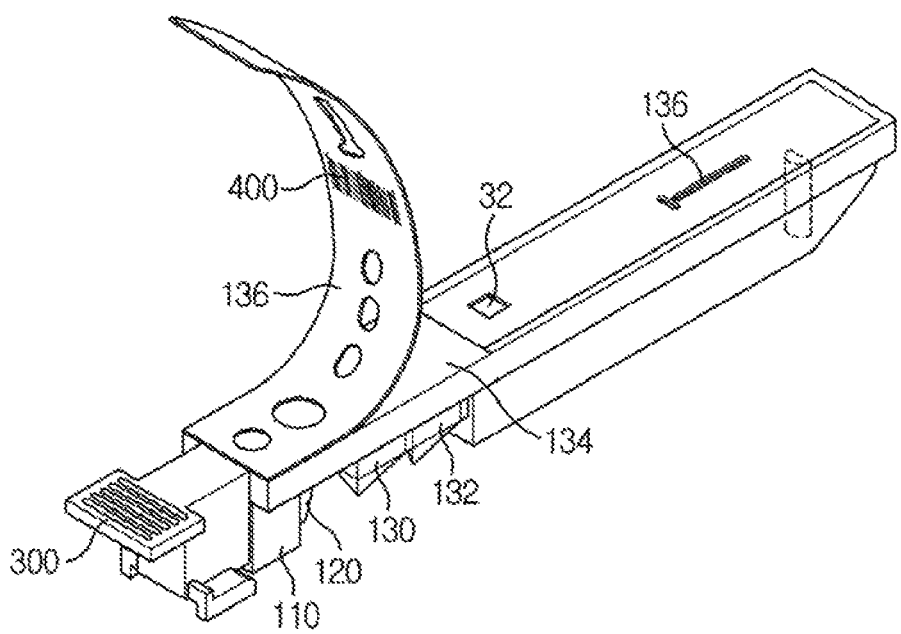
FIG. 5B is a schematic diagram of a perspective view of a multi-well cuvette comprising a second cover according to FIG. 5A with the second cover partially being detached from the cuvette.
Figure 6:
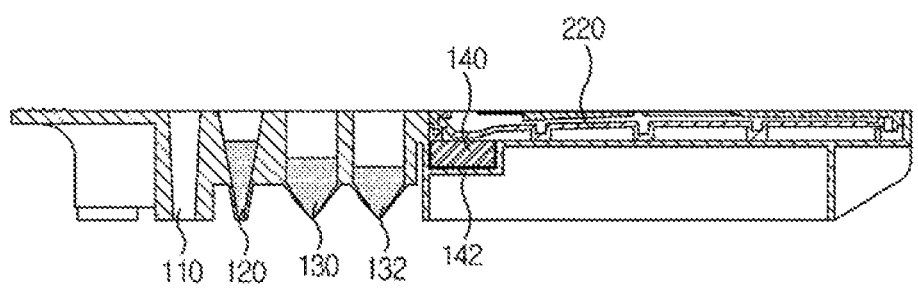
FIG. 6 is a sectional view taken along the line A-A' of FIG. 5A.

Referring to FIGS. 5A and 5B, the multi-well cuvette (1) of the present disclosure may further comprise a second cover (136) for covering the upper face or side of the cuvette to protect the surface of the cuvette from being damaged or contaminated and/or to identify the cuvette. In particular, the second cover covers all or part of the reaction part (100) and an analysis part (200). In this case, as depicted in FIG. 5B, a first cover (134) covering a first and a second reagent chambers are used and positioned underneath a second cover. As described hereinafter, for a collector such as a tip (T) for dispensing and/or taking liquid samples in and out of the chambers, or for reading the chromatographic results through a measurement window, holes are formed on the second cover at positions corresponding to each of the collector receiving or standby chamber (110), the biological sample chamber (120), the first reagent chamber (130), a second reagent chamber (132), the sample inlet (32) and the measurement window (34) so that the corresponding parts are exposed. Also the second cover may be peeled off before use or the present cuvette may be used with the second cover in place.

According to one embodiment of the present disclosure, the second cover may further comprise a barcode (400). As described hereinafter, the present multi-well cuvette may be used with a test device particularly with an automatic test device in which a sample dispensing, and a detection and reading of the reaction products are carried out in an automatic fashion in one device. In such cases, inserted into the device is an ID chip containing information regarding such as targets, materials and/or samples to be tested, standard curve information for quantitative analysis, and information for processing errors when the measured values are out of range. Bar codes provide such information as to match the multi-well cuvette with an appropriate ID chip.

The cartridge which may be employed in the present disclosure may have various dimensions and forms which are compatible with the detection part (210) of the present multi-well cuvette. In one embodiment, the present cartridge may have a rectangular shape and be manufactured with chemically inert various synthetic resins.

As depicted in FIG. 1, in the multi-well cuvette (1) of the present disclosure, a collector receiving or stand-by chamber (110), a liquid sample chamber (120), a reagent chamber (130, 132) and a detection part (210) are integrated into one device, the cuvette, and they are sequentially arranged in a row. In this case, although not depicted in FIG. 1, more than one row each row including the collector receiving or stand-by chamber (110), liquid sample chamber (120), reagent chamber (130, 132) and detection part (210) may be present. The multi-well cuvette (1) of the present disclosure as described above may be used with a certain test device. For example, the test device is a device operating in automatic in which a sample dispensing, and a detection and reading of the reaction products are carried out in an automatic fashion in one device.

The multi-well cuvette (1) of the present disclosure having the chambers arranged in a row as described above allows a simple and fast operation of the test device by requiring only a displacement on a straight line. Also test errors due to the mix-up of the reagents when multiple targets are tested at the same time may be reduced because the reagent chamber containing the appropriate reagent and the detection part to detect the reaction products are all provided being integrated into one cuvette obviating the need for separate reagent tubes. Also various targets can be analyzed in one device without changing the reagents.

Also the cost for manufacturing may be reduced since the multi-well cuvette (1) of the present disclosure has a simple structure in which a collector receiving or stand-by chamber (110), a liquid sample chamber (120), a reagent chamber (130, 132) and a detection part (210) are integrated into one device sequentially arranged in a row thus requiring a simpler manufacturing device.

The multi-well cuvette (1) of the present disclosure is disposable and may comprise a microtip (for example a micropipette tip having 2-1000 μl in volume). Thus simple devices without a system providing a reagent(s) and washing contaminant may be used with the present cuvette.

In one embodiment, the test device which may be used with the present multi-well cuvette is a device in which a sample and reaction product dispensing, and a detection and reading of the reaction products are carried out in an automatic fashion and is a device equipped with a means to dispensing or distributing the sample and the reaction product. The means to dispensing the sample and the reaction products which may be included in the device is able to move above the present cuvette along the x-axis of a collector receiving or stand-by chamber (110), a liquid sample chamber (120), a reagent chamber (130, 132) and a detection part (210). Such means includes an arm formed with a tip at one end and equipped with a pump for intake or discharge of liquid samples such as a biological sample, a reagent and/or reaction product for dispensing or distributing them. Such tips are inserted into a microtip with a various volume capacity such as 10 μl, 100 μl, 200 μl, or 500 μl and used for dispensing and/or distributing liquid samples such as a biological sample, a reagent and/or reaction product. The collector receiving or stand-by chamber (110) have a top which is opened so that a tip in the test device can be inserted thereto and used for collecting liquid samples. That is, the collector receiving or stand-by chamber (110) and biological sample chamber (120) have a top that is opened (112, 114) so that the tip can be inserted thereto. Also engagement with a microtip, and dispensing/distributing liquid sample may also be performed through the opening member (112, 114).

In one embodiment of the present disclosure, the multi-well cuvette of the present disclosure may further comprise a cover covering all or part of the upper surface or upper side of the reagent chamber (130) and the detection part (210).

The cover according to the present disclosure separates and protect the inner spaces defined by the reagent chamber (130) and the elements constituting the detection part (210) from being influenced by the outside environment. Accordingly, the reagent present in the reagent chamber (130) and the reaction product in the detection part (210) can be protected from being contaminated or decomposed by an unintentional exposure to the outside environment, which leads to increasing the reliability of the test results.

In such cases, the first cover (134) is placed on the reagent chamber (130). And the first cover (134) may have a thin membrane structure so that a test device with a predetermined tip can bore or perforate the membrane and penetrate into the appropriate chamber. That is, the reagent chamber (130) is covered with a first cover (134) that is configured to have a thin membrane structure so that the first cover (134) is perforated by a tip equipped with a collector such as a microtip penetrating into the chamber. For example the first cover (134) is a thin membrane formed of a metal such as aluminum or a synthetic resin such as plastic without being limited thereto.

Particularly, the present multi-well cuvette (1) further comprise a connecting jig (300) at one end thereof. In one embodiment, the jig (300) may be placed at an end of the cuvette extending in a length direction as illustrated in FIG. 1. But the embodiment is not limited thereto and the jig may be placed at any position as long as it exerts a function desired.

By employing the jig (300), the changing or disposal of the present multi-well cuvette (1) after a test is finished may be facilitated. That is, the multi-well cuvette (1) of the present disclosure may be removably installed in a test device through the jig (300) facilitating the test using the present multi-well cuvette.

Figure 3:
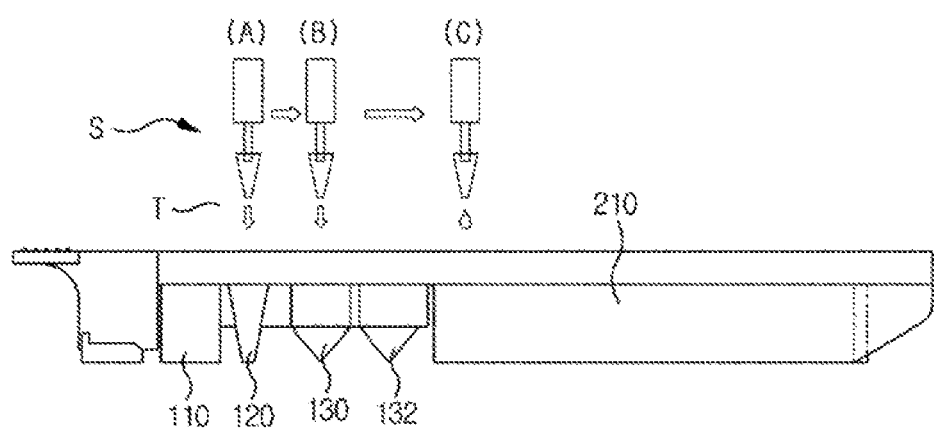
FIG. 3 is a schematic diagram illustrating a procedure of a test using the multi-well cuvette according to one embodiment.

Referring to FIG. 3, a process of a test using the present multi-well cuvette is described in detail.

Firstly, a tip (T) installed in a test device (S) moves downward through the open member (112) and inserts itself into a collector such as microtip in the collector receiving or stand-by chamber (110). Then the tip (T) moves upward and along X-axis to the sample chamber (120) at which the tip is moving downward to collect a sample in the sample chamber (120) as shown in (A).

Next, shown as (B), the tip with the sample is moving upward and along X-axis to the reagent chamber (130) at which the tip is moving downward to dispense the sample collected in the reagent chamber (130) and to mix and start a reaction with a reagent contained in the reagent chamber (130).

Finally, shown as (C), then the reaction product in the reagent chamber (130) is collected by the tip by moving in the same way as described above and loaded into the analysis part (200) through the sample inlet (32). In this case, the detection part (200) comprises a chromatographic cartridge (220) having a strip (20) for a lateral flow assay and the reaction product is introduced into the sample well of the cartridge from which the reaction product migrates to and is developed through the strip to produce an appropriate signal depending on the capture molecule attached on the strip and the labeling materials employed. The signal is detected through the measurement window formed on the cartridge (220) by a reader in the test device.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the inventive concept as defined by the following claims.

Unless otherwise defined, all the terms (including technical and scientific terms) used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

DESCRIPTION OF NUMERALS

1: Multi-well cuvette
100: Reaction part

110: Collector receiving or stand-by chamber
112, 114: Open member
120: Sample chamber
130: First reagent chamber
132: Second reagent chamber
134: First cover
136: Second cover
138: Magnetic or separation member
140: Magnet
142: Magnet holder
200: Analysis part
210: Detection chamber
220: Cartridge
300: Jig
400: Barcode

What is claimed is:

1. A cuvette comprising:
a jig;
a reaction part comprising a sample chamber configured to accommodate a liquid sample and a reagent chamber configured to accommodate a reagent for reaction with the liquid sample therein; and
an analysis part comprising a reaction product well configured to hold a liquid reaction product and a chromatographic strip extending between a first strip end and a second strip end,
wherein the jig, the sample chamber, the reagent chamber, the reaction product well, the chromatographic strip are integrated in a cuvette body;
wherein the sample chamber, the reagent chamber and the reaction product well are arranged between the jig and the first strip end of the chromatographic strip such that the sample chamber, the reagent chamber and the reaction product well are aligned in a direction along extension of the chromatographic strip from the first strip end toward the second strip end,
wherein the cuvette is configured to permit the liquid reaction product, when applied to the reaction product well, to flow to the first strip end of the chromatographic strip for a later flow assay in which the liquid reaction product further flows in the chromatographic strip in the direction from the first strip end toward the second strip end.

2. The cuvette of claim 1, wherein the sample chamber, the reagent chamber and the reaction product well are serially arranged along the direction from the first strip end toward the second strip end.

3. The cuvette of claim 1, further comprising:
a sample opening formed through the cuvette body immediately above the sample chamber; and
the reagent opening formed through the cuvette body immediately above the reagent chamber.

4. The cuvette of claim 1, wherein the reagent chamber is referred to as a first reagent chamber, and the reagent is referred to as a first reagent, wherein the cuvette further comprises a second reagent chamber formed in the cuvette body and containing a second reagent, wherein the second reagent chamber is located between the sample chamber and the reaction product well.

5. The cuvette of claim 1, wherein the reagent chamber is referred to as a first reagent chamber, and the reagent is referred to as a first reagent, wherein the cuvette further comprises a second reagent chamber formed in the cuvette body and containing a second reagent, wherein the second reagent chamber is located between the first reagent chamber and the reaction product well.

6. The cuvette of claim 1, wherein the reagent chamber is referred to as a first reagent chamber, and the reagent is referred to as a first reagent, wherein the cuvette further comprises a second reagent chamber formed in the cuvette body and containing a second reagent, wherein the sample chamber, the first reagent chamber and the second reagent chamber are arranged in order along the direction from the first strip end toward the second strip end.

7. The cuvette of claim 1, further comprising a detection chamber and a chromatographic cartridge, wherein the detection chamber is formed in the cuvette body and configured to receive the chromatographic cartridge therein for integrating with the cuvette body, wherein the chromatographic cartridge comprises the reaction product well and the chromatographic strip therein.

8. The cuvette of claim 7, wherein the chromatographic cartridge comprises at least one structure configured to permit the liquid reaction product to flow to the first strip end of the chromatographic cartridge.

9. The cuvette of claim 7, wherein the sample chamber, the reagent chamber and the reaction product well are serially arranged along the direction from the first strip end toward the second strip end.

10. The cuvette of claim 7, wherein the chromatographic cartridge is elongated along the direction from the first strip end toward the second strip end.

11. The cuvette of claim 7, wherein the chromatographic cartridge further comprises an inlet for accessing the reaction product well.

12. The cuvette of claim 1, wherein the reaction product well and the first strip end of the chromatographic strip are in fluid communication such that the liquid reaction product flows to the first strip end of the chromatographic strip.

13. The cuvette of claim 7, wherein the chromatographic cartridge further comprises a top cover covering the chromatographic strip and a measurement window formed through the top cover, wherein the measurement window is over the chromatographic strip and elongated along the extension of the chromatographic strip.

14. The cuvette of claim 1, further comprises a magnet placed in the vicinity of the reaction product well for magnetically attracting and hindering magnetic beads contained in the liquid reaction product from flowing through the chromatographic strip when the liquid reaction product containing magnetic beads is applied to the reaction product well.

15. The cuvette of claim 1, further comprising a collector receiving chamber configured to accommodate a tip of a device configured for taking the liquid sample from the sample chamber and for dispensing the liquid sample into the reagent chamber.

16. The cuvette of claim 15, further comprising a first cover covering an opening for the reagent chamber, wherein the first cover is formed of a membrane for the tip to penetrate and move into the reagent chamber.

17. The cuvette of claim 16, further comprising a second cover covering at least part of the first cover.

* * * * *